United States Patent
Patton (10) Patent No.: US 6,292,688 B1
(45) Date of Patent: Sep. 18, 2001

(54) METHOD AND APPARATUS FOR ANALYZING NEUROLOGICAL RESPONSE TO EMOTION-INDUCING STIMULI

(75) Inventor: Richard E. Patton, Colorado Springs, CO (US)

(73) Assignee: Advanced Neurotechnologies, Inc., Colorado Springs, CO (US)

(*) Notice: Subject to any disclaimer, the term of this patent is extended or adjusted under 35 U.S.C. 154(b) by 732 days.

(21) Appl. No.: 08/608,440

(22) Filed: Feb. 28, 1996

(51) Int. Cl.$^7$ ........................................... A61B 5/04
(52) U.S. Cl. ........................ 600/544; 600/545; 600/300
(58) Field of Search .................... 128/731, 732, 128/630; 600/544, 545, 300

(56) References Cited

U.S. PATENT DOCUMENTS

| | | | |
|---|---|---|---|
| Re. 34,015 | * 8/1992 | Duffy | 128/731 |
| 4,649,482 | * 3/1987 | Raviv et al. | 128/731 |
| 4,736,307 | * 4/1988 | Salb | 128/731 |
| 4,744,029 | * 5/1988 | Raviv et al. | 128/731 |
| 4,789,235 | 12/1988 | Borah et al. . | |
| 4,794,533 | 12/1988 | Cohen . | |
| 4,815,474 | * 3/1989 | Duffy | 128/731 |
| 4,862,359 | * 8/1989 | Trivedi et al. | 128/731 |
| 4,955,388 | 9/1990 | Silberstein . | |
| 5,024,235 | 6/1991 | Ayers . | |
| 5,113,870 | 5/1992 | Rossenfeld . | |
| 5,137,027 | 8/1992 | Rosenfeld . | |
| 5,230,346 | 7/1993 | Leuchter et al. . | |
| 5,243,517 | 9/1993 | Schmidt et al. . | |
| 5,331,969 | * 7/1994 | Siberstein | 128/731 |
| 5,339,826 | 8/1994 | Schmidt et al. . | |
| 5,392,788 | 2/1995 | Hudspeth . | |

* cited by examiner

Primary Examiner—Michael Peffley
(74) Attorney, Agent, or Firm—Vedder Price Kaufman & Kammholz (57) ABSTRACT

A method of determining the extent of the emotional response of a test subject to stimului having a time-varying visual content, for example, an advertising presentation. The test subject is positioned to observe the presentation for a given duration, and a path of communication is established between the subject and a brain wave detector/analyzer. The intensity component of each of at least two different brain wave frequencies is measured during the exposure, and each frequency is associated with a particular emotion. While the subject views the presentation, periodic variations in the intensity component of the brain waves of each of the particular frequencies selected is measured. The change rates in the intensity at regular periods during the duration are also measured. The intensity change rates are then used to construct a graph of plural coordinate points, and these coordinate points graphically establish the composite emotional reaction of the subject as the presentation continues.

22 Claims, 4 Drawing Sheets

METHOD AND APPARATUS FOR ANALYZING NEUROLOGICAL RESPONSE TO EMOTION-INDUCING STIMULI

BACKGROUND OF THE INVENTION

The present invention relates generally to methods and apparatus for neurological testing, and more particularly, to methods and apparatus for determining the emotional state of an individual over the period of time during which that individual is being exposed to time-varying stimuli. While in one respect the invention applies to determining the neurological, psychological, or emotional response of an individual to test stimuli, in many instances, the invention is applicable to using individuals to test a program containing certain stimuli, in order to determine whether such a program will subsequently create favorable responses in other individuals of similar sociocultural-economic makeup.

One of the most practical applications of the method and apparatus with which the invention is presently concerned is that of consumer response testing. Accordingly, this aspect of the method will be discussed immediately herein, while a discussion of other applications and purposes implicit in the invention will be set out elsewhere herein.

In the United States, and elsewhere throughout the world, advertising is heavily used to promote consumer, commercial and industrial products. It is almost universally accepted that, as between or among products which are generally similar to one another in content, price, or quality, successful advertising can help a particular product achieve much greater market penetration and financial success than an otherwise similar product. Advertising, and particularly consumer advertising, although a multi-billion dollar industry in the United States alone, is an area wherein workers find it extremely difficult to create and reproduce what prove to be consistently successful advertising campaigns, themes, or other materials. It is likewise accepted that while it is often easy to predict that response to a particular proposed advertisement or campaign will be unfavorable, it is not known how to create individual advertisements and/or campaigns which can virtually be assured of success on a consistent basis.

Moreover, while it is not always difficult to discover how to make advertising which may simply interest or amuse potential consumers, or to create advertising that consumers will remember, it is often quite another thing to create an advertisement or campaign which succeeds in actually motivating potential consumers to become actual consumers. There are numberless instances known to the advertising community wherein advertising for a particular product is well recognized, is associated with the product and creates a lasting and favorable impression on the consumer as regards the manner in which the advertisement is presented. Yet, as far as can be accurately measured, many such ads fail to impel viewers to use more of such product, or favor it over that of a competitor.

The advertising industry has also recognized that an advertisement must serve the functions referred to above and that this is normally done in individual stages. Thus, the agencies realize that the creative message must attract the user in some way, and preferably, convey a message or impression about the product as well as contain a command or "call to action." However, the particular emotion required to secure attention may defeat the purpose of the message or compromise the call to action portion. Likewise, a part of the message, in an attempt to be clever, may offend some viewers or, in an attempt to gain attention, may appear more frivolous than intended.

Hence, it is very difficult on a prospective basis to predict whether a viewer will see a commercial as imaginative and clever on the one hand or frivolous and incredible on the other, when the differences in such presentation are very slight. Similarly, an overly detailed message may appear to be too clinical or perhaps worse, condescending, while another message may be non-offensive but also non-informing. The differences in comprehensional and emotional states of advertising material viewers may be slight but extremely important.

Hence, among all the possible advertisements that might be produced in the hopes of generating a successful consumer response, even where a large number of efforts are summarily dismissed or weeded out, the persons preparing the advertising and the companies using the advertising for promotional purposes simply cannot be sure within narrow limits as to whether particular advertising material will be a success in the marketplace. Accordingly, it is common to find that long after decisions are made and expenditures incurred in pursuit of presenting a particular advertisement (or theme or campaign of advertisements), that such efforts have simply not been successful, in that the campaign failed to produce sales in amounts proportionate to the expenditure of effort and money.

It is believed that an ideal advertisement is one which can be comprehended by the viewer or listener, which contains an inherently credible message, and which contains an imperative or call to action which will stimulate the viewer or listener to purchase the product in question. The advertising industry has for decades accepted the principle that a simple presentation of an advertising message in cold, hard, clear and logical terms is usually insufficient to induce a prospective purchaser to buy a particular product.

Even if viewers were highly analytical, (and it is accepted that most consumers are not), there is still the problem of differentiation between products whose characteristics are either highly subjective or whose quantitative differences are very minute vis-à-vis those of a competitor. Thus, the flavor of a beer or a hamburger, or the appearance of an article of clothing, is simply incapable of being quantified and presented in analytical terms. Even if such were the case, the question of motivation to buy a selected product would still remain.

Consequently, it has come to be accepted that in a great majority of cases, with a few possible exceptions not pertinent here, the decision to buy products is an emotional one in one sense or another. The presence of such emotion does not imply that the choice is irrational, but merely that it meets a need that the subject perceives himself to have, or will have, at the time of purchase. Whether the emotional response is one of self-satisfaction, one of belief that an intelligent choice has been made or that the choice will create a favorable appearance, image or other response in the buyer is not particularly important. According to the invention, it is believed that discovering and qualitatively and quantitatively analyzing the actual emotional response of a subject is the key to correlation between an advertising presentation and a successful sale of the product.

Referring again to the subject of advertising response, it would be ideal if people preparing advertisements were able to put themselves in the shoes, so to speak, of the particular customer. However, while certain advertising agencies are able to use the talents of creative personnel who are successful more often than not, a high degree of correspondence between choosing and presenting a particular ad and achieving product sales is simply not available on a consistent basis.

Of course, for many years, efforts have been made to determine consumer reactions or consumer response to advertising by different methods of obtaining "feedback." These include many forms of interviewing or testing consumers, either individually or in groups. Programs which are commonly used consist of "focus groups" made up of subjects who are shown different materials and asked about their response to the materials. Other programs comprise telephone interviews with members of a selected group or universe. These efforts continue, but the results they obtain are often questionable in terms of value to the advertiser.

The industry, having accepted that the word of a person creating an ad is insufficient to insure success, and knowing that a product proprietor does not consistently hold the key to identifying and pursuing advertising successes, has relied significantly on focus groups and questionnaires, those research techniques, including the use of reaction surveys, which are now in common use.

The answers of persons who are questioned during response testing, however, are notoriously unreliable as an indicator of their true emotions. For years, workers in the field have realized that, for any number of reasons, test subjects tend not to recall, or to be indirect, evasive or simply inaccurate in describing their emotional response to a particular stimulus. Thus, even if these subjects were able to recall accurately their emotional state at the time of perceiving stimuli, the likelihood that they could recall and identify an exact emotional state or set of feelings, particularly where the emotions change rapidly, is very unlikely.

This is thought to be attributable to a number of causes, including inadequate vocabulary and possible protection of the ego of the test subject vis-à-vis the tester. Thus, many test subjects are reluctant to disclose that they are more emotional than seems prudent, particularly when disclosing such an emotional state to a virtual stranger. More important than the vagaries of recollection and characterization of emotions at a particular time is the comparatively recent realization that during an advertising presentation, (for example, a television commercial lasting 15 to 30 seconds), the subject undergoes a large number of emotional state changes. Therefore, asking the test subject to recall each such state and its comparative intensity is simply asking the impossible.

According to the present invention, tests have shown that a subject might undergo as many as 5, 10 or even 15 changes in emotional response while watching a commercial that lasts only 15 to 30 seconds. Because emotional states vary, and change with great rapidity in intensity and/or polarity, (or simply disappear altogether), it has been realized that a higher quality of emotional states analysis is required for response testing to achieve maximum effectiveness.

According to the present invention, it is believed that if a second-by-second recording could be made of the emotional state of a viewer of a television commercial, and if it could be shown how such emotional changes correspond to the exact subject being presented at any one increment of time, successful or improved commercials could be created with regularity. Thus, and referring to the previous discussion, if a particular subject were to report that he were "turned off" by a particular commercial, then a worker might consider that the commercial was a failure. However, it is at least possible if not likely that certain features of that exact same commercial might have had strong attraction for the viewer, and it was another aspect or portion of that same commercial that "turned off" the subject. If this were actually the case, then the attractive parts of any given presentation could be retained and unsatisfactory portions could be eliminated or modified. By the same token, subject matter creating a strong positive response could be utilized to the greatest possible extent and could be repeated and/or incorporated in other materials.

It has been established through medical research, including that carried out by the Naval Aerospace Medical Research Laboratory, that EEG recordings reflect the fact and manner of information processing by an individual in a general or global sense. Thoughts, feelings, perceptions, and instructions all are processed in the brain as information, the reflection of which processing is detectable using EEG methods.

According to now accepted principles, the electrical activity incident to brain function can be detected and measured. Electroencephalography ("EEG") is the science of measuring brain waves. Using research information which correlates brain wave activity of a particular frequency and character to a particular emotion makes it possible to discriminate among polar opposite emotions as well as closely allied emotions. In the present context, the primary emotions (and their polar opposites) with which the invention is concerned are those of pleasure, arousal, dominance, abstract comprehension and pictorial comprehension.

The emotion of pleasure is self-explanatory and relates to enjoyment of what is being perceived. Abstract and pictorial comprehension are essentially self-explanatory. Arousal refers to an awakening of interest in the subject matter and dominance, or its polar opposite, submissiveness, refers to receptivity or openness to ideas or suggestions. Thus, a person whose emotions are in a dominant state is not open to suggestion, and a person in a low state of arousal lacks interest in an idea.

Referring to the mechanics of measuring emotion, the invention utilizes what is termed a circumplex model for correlating neurophysiological manifestations to emotions. The circumplex model has a pair of orthogonal axes intersecting at an origin. The emotions are displayed as points arranged in a circle about the origin, with diametrically opposed points representing polar opposite emotions and adjacently displayed points representing emotions that differ from each other more by shading than by character. Graphs are made by plotting positions on the circumplex and the character of the subject emotion is established by mathematical modeling ("non-linear analysis") based on brain wave frequency and intensity.

Inasmuch as an important aspect of the invention concerns the emotional changes undergone by the subject in response to presentation and detection of stimuli, the graphical or mathematical models are utilized to establish emotional conditions at various times and track the history of the emotional changes in relation to the stimuli. These methods then enable a comparison to be made between presented subject matter and a true, objective emotional response in the test subject. In general, this "non-linear dynamic" method establishes the relationship or linkage between EEG data and brain function, and hence, emotion. Research workers can convert data taken during observation of stimuli by a subject into an accurate, second-by-second record of the emotional response of the test subject to the stimuli being presented. While the manner of analysis will be described in greater detail, the invention has been successfully practiced by measuring the amplitudes of EEG waves at up to five individual frequencies, including 8 Hz (cycles per second), 13 Hz, 16 Hz, 18 Hz and 26 Hz. At each given frequency, the amplitude of the signal is indicative of the strength of a particular emotional component.

Comparing the values of a given component on one scale to the value of a component taken on another scale enables the tester to establish an accurate, all-around emotional state at a given instant. The general state determined by comparing two values is then refined into an exact emotional profile using comparisons of other values as auxiliary or follow-on steps. The invention holds out the promise of correlating these measurements of emotional intensity and characterization to a series of exactly defined emotions and, equally important, the changes and change rates in these emotions as the subject is exposed to stimuli, typically one or more audio-visual presentations. These changes and rates are sometimes called "composite emotional forces."

In view of the failure of the prior art to provide an effective method of determining the emotional response of a test subject of the content of time-varying stimuli, it is an object of the present invention to provide a method and apparatus for this purpose.

Another object of the invention is to provide a test method which will enable a correlation to be established between the actual emotional state of a subject being measured and the content of a message or other stimulus being presented to the subject at any given time interval within the presentation.

Yet another object of the invention is to provide an improved method and apparatus for analyzing the effectiveness of actual or proposed advertising copy or other presentational material.

A further object of the invention is to provide a method for enabling emotions and emotional changes and change rates in a test subject to be determined by directly measuring several components of the emotion and plotting the components to characterize the emotion in an accurate way.

A still further object of the invention is to provide a method of charting a sequence of emotional response signals in graphically visible form so as to facilitate analysis of an overall emotional response to predetermined stimuli.

An additional object of the invention is to provide a method of classifying the acceptability of advertising content by predetermining its emotional impact on test subjects before determining the final form which such advertising will take.

Another object of the invention is to utilize a method of direct testing of emotional components in selected individuals as a way of measuring the anticipated response to a given advertisement by individuals in the general population, and hence to greatly increase the predictability that such advertisements will succeed.

Yet another object of the invention is to provide a method that will minimize or eliminate waste of advertising by preventing advertisers from presenting ads that are unlikely to succeed, based on predictions using direct emotional response test subjects.

A further object of the invention is to provide a series of correlational tools to associate individual emotional response components, both in character and intensity, with particular brain wave activities for the purpose of accurate emotional response testing.

The invention achieves the foregoing and other objects and advantages by positioning a test subject to observe the selected stimuli for a given duration, establishing a path of communication between the subject and a brain wave detector/analyzer, determining at least two frequencies at which brain waves corresponding to particular emotional component intended to be analyzed are generated, presenting stimuli to a test subject, recording the amplitudes of brain waves at particular frequencies and thereafter comparing the amplitude changes in the different brain wave frequency bands, over the duration of the presentation, and thereby determining the overall and particular emotional responses of the test subject to one or more of the various individual portions of the presentation containing the stimuli.

The invention also achieves its objects and advantages by providing a method of emotional analysis that includes determining which one or more emotional scales are important to the subject matter of a test or other analysis, determining the brain wave frequencies which characterize such one or more emotional scales and wherein the brain waves vary in intensity in relation to the degree of emotional response of a subject to input stimuli in the form of a given presentation, exposing the subject to a presentation having a particular, predetermined content, noting the ongoing variations in intensity of the brain waves of the subject at each of at least two measured frequencies, and thereafter calculating a characteristic actual multiscalar response of the individual to the content of the presentation for analyzing the response of the subject during or after a given presentation.

The manner in which the foregoing and other objects and advantages of the invention are achieved in practice will become more clearly apparent when reference is made to the following detailed description of the preferred embodiments of the invention set forth by way of example and shown in the accompanying drawings, charts and appendices wherein like reference numbers or legends indicate corresponding parts throughout.

DESCRIPTION OF THE PREFERRED EMBODIMENTS OF THE INVENTION

Before referring to the particular form of data developed by the use of the inventive method, and the methods of displaying and analyzing such data, a brief description will be given of a typical electroencephalographic ("EEG") brain wave detector and analyzer of the type used with the invention. Thus, referring now to FIG. 1, there is shown in schematic form a detector-analyzer apparatus generally designated 10 of the invention positioned with pick up or test points positioned on the head portion generally designated 12 of a test subject.

Figure 1:
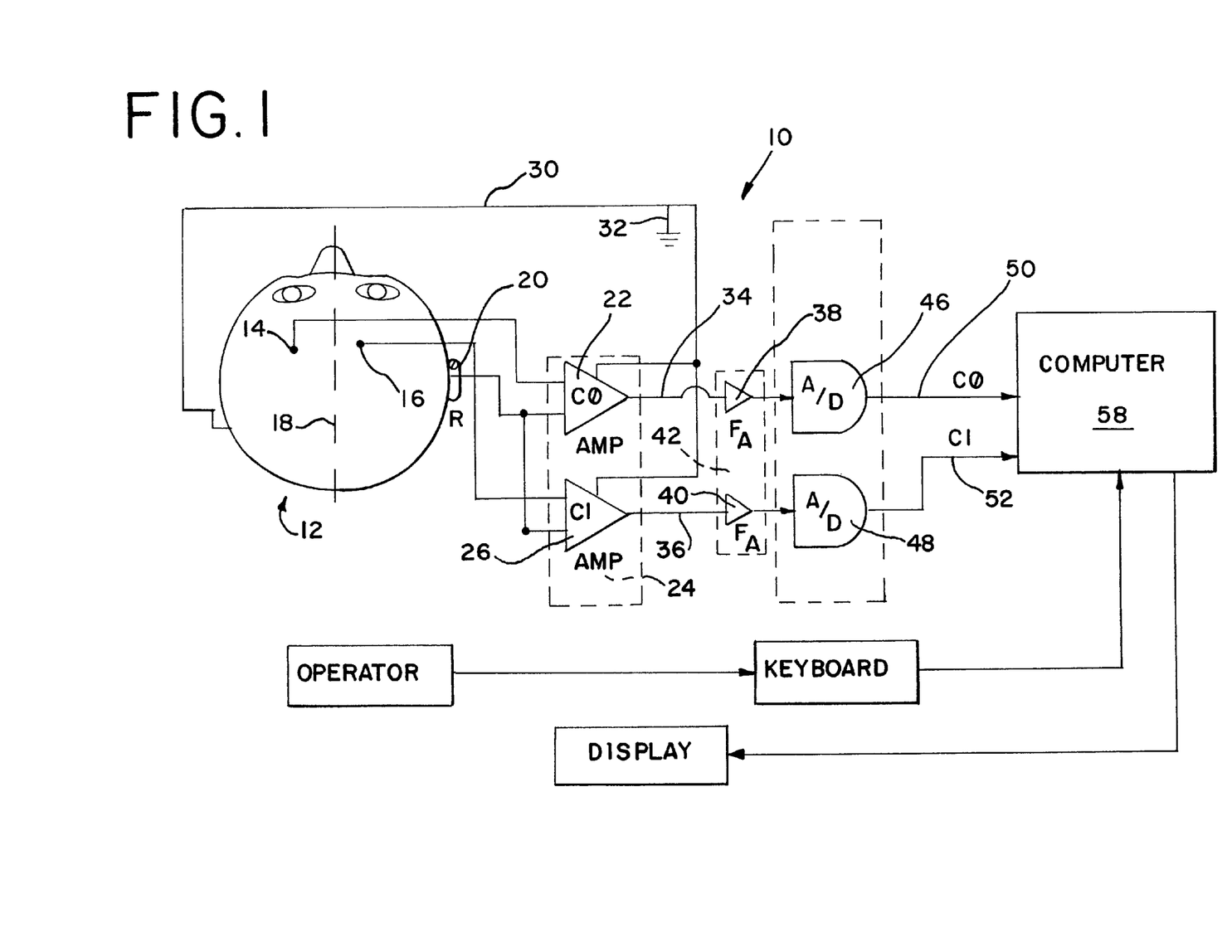
FIG. 1 is a schematic view of a part of the apparatus of the invention, showing the manner of acquiring and processing brain wave signals from a subject whose emotions are to be measured.

According to the invention, left and right hand test points 14, 16 are selected, one on either side of the midline 18 of the scalp of the subject 12. The head is fitted with cup-type electrodes coated with an electrically conductive gel, as is conventional and known to those skilled in the art.

An electrical reference connection is selected, in this case on the right side ear lobe 20. Further in accordance with the invention, an operational amplifier receives and amplifies EEG signals that are transformed, analyzed and recorded and/or displayed. Accordingly, the output from one scalp point 14 and from the reference point are sent to the input terminals of a first operational amplifier 22 forming part of an operational amplifier bank 24. A second operational amplifier 26 receives signals from the other scalp point 16 and the reference 20. Each amplifier has a common feedback connection 30 which is grounded, as at 32.

The respective outputs 34, 36 of the amplifiers 22, 26 are fed to individual, high-gain biologic amplifiers 38, 40 within a biologic amplifier block 42, typically possessing a gain of 50,000 to 200,000 with suitable bandpass filters enabling signals of 0.3 to 45 Hz to be passed and the remainder to be blocked.

The respective outputs of the biologic amplifiers 38, 40 are passed to analog-to-digital (A/D) converters 46, 48 which are interfaced with a digital microcomputer such as a microcomputer made by Commodore or IBM, for example. The output signals emerging from the converters 46, 48 are seen in lines 50, 52.

Frequency information is calculated using transforms such as Fast Fourier Transforms ("FFT") or Hartley or Wavelet transforms. The presently preferred transforms are Wavelet transforms which minimize the informational loss sometimes associated with FFT transforms.

With the computer 58 being properly programmed by the operator, displays of and/or a recording can be made of the intensity or amplitude of ongoing brain wave activity at each of five selected frequencies, the reasons for the selection of which are discussed herein.

Bearing in mind that the inventive concept relates to making and refining electrical measurements that are indicative of emotional states, reference will now be made to classifications of various emotions in a manner whereby the identity of the emotion is determined by analyzing a series of graphs or charts having geometric characteristics. The invention uses an arrangement of the representation of various emotions in a form which is useful from the standpoint of creating models or representations for purposes of analysis.

Figure 2:
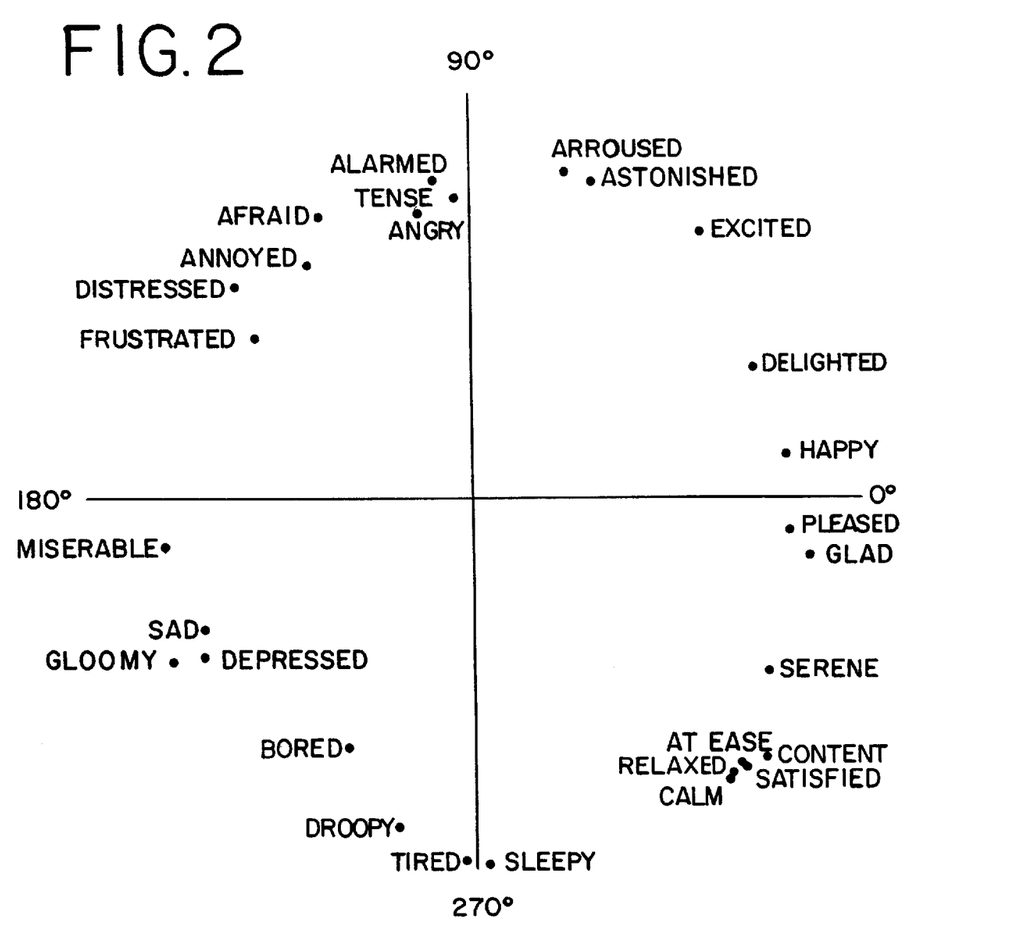
FIG. 2 is a graphic representation illustrating what is termed a circumplex of emotions, arranged about a graphic origin.

Referring now to FIG. 2. for example, there is shown what is termed a "Circumplex of Emotions."

In the expression "circumplex" as used herein simply means a graph, chart or the like wherein emotions are displayed around a center point or origin, and lie along or between two orthogonally arranged axes. A particular emotion is given a position on the graph in keeping with the extent to which it is influenced by the presence of one other emotion. The axes denote polarity, in that opposite positions on the graph show generally opposite emotions. Moreover, there are two axes because the graph compares intensity on two scales simultaneously. In the case of FIG. 2, the X-axis shows the emotions of pleasure-displeasure, or pleasure/sadness, while the Y-axis denotes arousal or alarm and its polar opposite, sleepy, tired or bored.

The expression "multidimensional scaling" as applied to FIG. 2 simply means that the pleasure (or other) scale is compared to the arousal (or other) scale, and the extent to which both emotions are present or absent will graphically determine where the resultant data point is positioned on the graph. FIG. 2 is sometimes referred to as the Mehrabian-Russel Paradigm.

Bearing in mind that each primary emotion has a polar opposite, and that the amplitude of brain waves at any particular frequency is never zero or less than zero, the polar opposite of any particular primary or tested-for emotion is indicated by minimal (or zero) amplitude. For graphic purposes, therefore, the origin is a starting or "neutral" point that is usually a certain number of units above zero, i.e., halfway between zero and the maximum anticipated attainable value. The amplitude used in these graphs and charts therefore represents the degree to which the emotion in question exceeds or falls below a neutral level.

The value in relation to the neutral point or reference represents the intensity of the emotion. According to the invention, because an overall emotional state is a composite of many factors, numerous charts are made for a final graphic non-linear analysis. This is done by comparing readings on one scale to readings on another scale. Where a more complex profile is desired, several scales are used. In some cases, it is desired to use as many as all possible combinations of those scales, taken two at a time. For example, the amplitude at a given frequency representing one emotional scale is plotted against the amplitude at another frequency representing another scale. Using pleasure and arousal as examples, pleasure intensity at a given time is compared to arousal intensity at that time. Then, pleasure and dominance are used, etc. In many, if not most cases, readings are made at frequent intervals, for example, just one or two seconds apart. In other cases, as amplified below, longer intervals or epochs are selected. The use of the computer permits tracking and recording of five frequencies simultaneously.

Using the two selected frequencies of 8 Hz and 16 Hz as corresponding respectively to pleasure and arousal, by way of example, a first "X-Y" or two-dimensional plot is made. A resultant point derives from the intensity of values on these two scales. This plot point has an angular component that indicates its qualitative nature and a radial component indicating its intensity. The qualitative character is determined by comparison with a known angle/description or circumplex chart such as that described by Plutchik (noted below) in 1994.

The angle/description or circumplex chart presently uses a refined or extended and then modified version of the Mehrabian-Russel Paradigm, in this case what are termed "adjusted" Plutchik Placements. Referring now to Table 1, there are listed an entire population of emotion terms, each having a characteristic angle from the origin, as follows:

TABLE 1

Angular Placement for a Population of Emotion Terms

| Emotion | Angular Placement |
| --- | --- |
| Accepting | 0.0 |
| Agreeable | 5.0 |
| Serene | 12.3 |
| Cheerful | 25.7 |
| Receptive | 32.3 |

TABLE 1-continued

Angular Placement for a Population of Emotion Terms

| Emotion | Angular Placement |
| --- | --- |
| Calm | 37.0 |
| Patient | 39.7 |
| Obliging | 43.3 |
| Affectionate | 52.3 |
| Obedient | 57.7 |
| Timid | 65.0 |
| Scared | 66.7 |
| Panicky | 67.7 |
| Afraid | 70.3 |
| Shy | 72.0 |
| Submissive | 73.0 |
| Bashful | 74.7 |
| Embarrassed | 75.3 |
| Terrified | 75.7 |
| Pensive | 76.7 |
| Cautious | 77.7 |
| Anxious | 78.3 |
| Helpless | 80.0 |
| Apprehensive | 83.3 |
| Self-conscious | 83.3 |
| Ashamed | 83.3 |
| Humiliated | 84.0 |
| Forlorn | 85.0 |
| Nervous | 86.0 |
| Lonely | 88.3 |
| Apathetic | 90.0 |
| Meek | 91.0 |
| Guilty | 102.3 |
| Sad | 108.5 |
| Sorrowful | 112.7 |
| Empty | 120.3 |
| Remorseful | 123.3 |
| Hopeless | 124.7 |
| Depressed | 125.3 |
| Worried | 126.0 |
| Disinterested | 127.3 |
| Grief-stricken | 127.3 |
| Unhappy | 129.0 |
| Gloomy | 132.7 |
| Despairing | 133.0 |
| Watchful | 133.3 |
| Hesitant | 134.0 |
| Indecisive | 134.0 |
| Rejected | 136.0 |
| Bored | 136.0 |
| Disappointed | 136.7 |
| Vacillating | 137.3 |
| Discouraged | 138.0 |
| Puzzled | 138.3 |
| Uncertain | 139.3 |
| Bewildered | 140.3 |
| Confused | 141.3 |
| Perplexed | 142.3 |
| Ambivalent | 144.7 |
| Surprised | 146.7 |
| Astonished | 148.0 |
| Amazed | 152.0 |
| Awed | 156.7 |
| Envious | 160.3 |
| Disgusted | 161.3 |
| Unsympathetic | 165.6 |
| Unreceptive | 170.0 |
| Indignant | 175.0 |
| Disagreeable | 176.4 |
| Resentful | 176.7 |
| Revolted | 181.3 |
| Displeased | 181.5 |
| Suspicious | 182.7 |
| Dissatisfied | 183.0 |
| Contrary | 184.3 |
| Jealous | 184.7 |
| Intolerant | 185.0 |
| Distrusful | 185.0 |
| Vengeful | 186.0 |
| Bitter | 186.0 |
| Unfriendly | 188.0 |
| Stubborn | 190.4 |
| Uncooperative | 191.7 |
| Contemptuous | 192.0 |
| Loathful | 193.0 |
| Critical | 193.7 |
| Annoyed | 200.6 |
| Irritated | 202.3 |
| Angry | 212.0 |
| Antagonist | 220.0 |
| Furious | 221.3 |
| Hostile | 222.0 |
| Outraged | 225.3 |
| Scornful | 227.0 |
| Unaffectionate | 227.3 |
| Quarrelsome | 229.7 |
| Grouchy | 230.0 |
| Impatient | 230.3 |
| Defiant | 230.7 |
| Aggressive | 232.0 |
| Sarcastic | 235.3 |
| Rebellious | 237.0 |
| Exasperated | 239.7 |
| Disobedient | 242.7 |
| Demanding | 244.0 |
| Possessive | 247.7 |
| Greedy | 249.0 |
| Wondering | 249.7 |
| Impulsive | 255.0 |
| Anticipatory | 257.0 |
| Boastful | 257.3 |
| Expectant | 257.3 |
| Daring | 260.1 |
| Curious | 261.0 |
| Reckless | 261.0 |
| Proud | 262.0 |
| Inquisitive | 267.7 |
| Planful | 269.7 |
| Adventurous | 270.7 |
| Ecstatic | 286.0 |
| Sociable | 296.7 |
| Hopeful | 298.0 |
| Gleeful | 307.0 |
| Elated | 311.0 |
| Eager | 311.0 |
| Enthusiastic | 313.7 |
| Interested | 315.7 |
| Delighted | 318.6 |
| Amused | 321.0 |
| Attentive | 322.4 |
| Joyful | 323.4 |
| Happy | 323.7 |
| Self-controlled | 326.3 |
| Satisfied | 326.7 |
| Pleased | 328.0 |
| Generous | 328.0 |
| Ready | 329.3 |
| Sympathetic | 331.3 |
| Content | 338.3 |
| Cooperative | 340.7 |
| Trusting | 345.3 |
| Tolerant | 350.7 |

Using the above angular placement chart (termed Plutchik Placements), a verbal or descriptive characteristic of each of scores of emotions can be assigned to a resultant point determined by the graphic method just described, i.e., a point arrived at by plotting the amplitudes of simultaneously measured signals on two selected frequencies. Maintaining the geometric analogy, angles 0–90° comprise the First Quadrant, 91–180° the Second Quadrant, etc. Please see FIG. 6 for an illustration of the quadrant locations.

Referring now to Tables 2 through 5 below, four tables are presented which contain the same subject matter as those in Table 1, except that the emotions that were once in Quadrant One are now in Quadrant Three. In other words, the former Plutchik values are "adjusted" by adding 180° to them, and all have now become the "adjusted Plutchik Placements," each being two quadrants away from its former value:

TABLE 2

Adjusted Plutchik Placements
Quadrant 1
Angle (Degrees)

| | |
|---|---|
| 1.3 | Revolted |
| 1.5 | Displeased |
| 2.7 | Suspicious |
| 3.0 | Dissatisfied |
| 4.3 | Contrary |
| 4.7 | Jealous |
| 5.0 | Distrustful |
| 5.0 | Intolerant |
| 6.0 | Vengeful |
| 6.0 | Bitter |
| 8.0 | Unfriendly |
| 10.4 | Stubborn |
| 11.7 | Uncooperative |
| 12.0 | Contemptuous |
| 13.0 | Loathful |
| 13.7 | Critical |
| 20.6 | Annoyed |
| 22.3 | Irrated |
| 32.0 | Angry |
| 40.0 | Antagonistic |
| 41.3 | Furious |
| 42.0 | Hostile |
| 45.3 | Outraged |
| 47.0 | Scornful |
| 47.3 | Unaffectionate |
| 49.7 | Quarrelsome |
| 50.0 | Grouchy |
| 50.3 | Impatient |
| 50.7 | Defiant |
| 52.0 | Aggressive |
| 55.3 | Sarcastic |
| 57.0 | Rebellious |
| 59.7 | Exasperated |
| 62.7 | Disobedient |
| 64.0 | Demanding |
| 67.7 | Possessive |
| 69.0 | Greedy |
| 69.7 | Wondering |
| 75.0 | Impulsive |
| 77.0 | Anticipatory |
| 77.3 | Boastful |
| 77.3 | Expectant |
| 80.1 | Daring |
| 81.0 | Curious |
| 81.0 | Reckless |
| 82.0 | Proud |
| 87.7 | Inquisitive |
| 89.7 | Planful |
| 90.7 | Adventurous |

TABLE 3

Adjusted Plutchik Placements
Quadrant 2
Angle (Degrees)

| | |
|---|---|
| 106.0 | Ecstatic |
| 116.7 | Sociable |
| 118.0 | Hopeful |
| 127.0 | Gleeful |
| 131.0 | Elated |
| 131.0 | Eager |
| 133.7 | Enthusiastic |
| 135.7 | Interested |
| 138.6 | Delighted |
| 141.0 | Amused |
| 142.4 | Attentive |
| 143.4 | Joyful |
| 143.7 | Happy |
| 146.3 | Self-Controlled |
| 146.7 | Satisfied |
| 148.0 | Pleased |
| 148.0 | Generous |
| 149.3 | Ready |
| 151.3 | Sympathetic |
| 158.3 | Content |
| 160.7 | Cooperative |
| 165.3 | Trusting |
| 170.7 | Tolerant |
| 180.0 | Accepting |

TABLE 4

Adjusted Plutchik Placements
Quadrant 3
Angle (Degrees)

| | |
|---|---|
| 185.0 | Agreeable |
| 192.3 | Serene |
| 205.7 | Cheerful |
| 212.3 | Receptive |
| 217.0 | Calm |
| 219.7 | Patient |
| 223.3 | Obliging |
| 232.3 | Affectionate |
| 237.7 | Obedient |
| 245.0 | Timid |
| 246.7 | Scared |
| 247.7 | Panicky |
| 250.3 | Afraid |
| 252.0 | Shy |
| 253.0 | Submissive |
| 254.7 | Bashful |
| 255.3 | Embarrassed |
| 255.7 | Terrified |
| 256.7 | Pensive |
| 257.7 | Cautious |
| 258.3 | Anxious |
| 260.0 | Helpless |
| 263.3 | Apprehensive |
| 263.3 | Self-conscious |
| 263.3 | Ashamed |
| 264.0 | Humiliated |
| 265.0 | Forlorn |
| 266.0 | Nervous |
| 268.3 | Lonely |
| 270.0 | Apathetic |

TABLE 5

Adjusted Plutchik Placements
Quadrant 4
Angle (Degrees)

| | |
|---|---|
| 271.0 | Meek |
| 282.3 | Guilty |
| 288.5 | Sad |
| 292.7 | Sorrowful |
| 300.3 | Empty |
| 303.3 | Remorseful |
| 304.7 | Hopeless |
| 305.3 | Depressed |
| 306.0 | Worried |
| 307.3 | Disinterested |

TABLE 5-continued

Adjusted Plutchik Placements
Quadrant 4
Angle (Degrees)

| | |
|---|---|
| 306.3 | Grief-stricken |
| 309.0 | Unhappy |
| 312.7 | Gloomy |
| 313.0 | Despairing |
| 313.3 | Watchful |
| 314.0 | Hesitant |
| 314.0 | Indecisive |
| 316.0 | Rejected |
| 316.0 | Bored |
| 316.7 | Disappointed |
| 316.3 | Vacillating |
| 318.0 | Discouraged |
| 318.3 | Puzzled |
| 319.3 | Uncertain |
| 320.3 | Bewildered |
| 321.3 | Confused |
| 322.3 | Perplexed |
| 324.7 | Ambivalent |
| 326.7 | Surprised |
| 328.0 | Astonished |
| 332.0 | Amazed |
| 336.7 | Awed |
| 340.3 | Envious |
| 341.3 | Disgusting |
| 345.6 | Unsympathetic |
| 350.0 | Unreceptive |
| 355.0 | Indignant |
| 356.4 | Disagreeable |
| 356.7 | Resentfull |

By arranging these in the graphic manner of FIG. 2, it will be noted that "revolted" and "displeased" are displayed around zero degrees relative to the origin, with their polar opposites, "happy" or "pleased" being displayed at a 180° location relative to the origin. "Adventurous" and "planful" are displayed near the 90° portion of this circular scale whereas the opposites of arousal, for example, meek, appear near 270°, in a graphically opposite location.

Emotions that lie between the two sets of axes are considered a composite of two of the basic emotions forming the axis plots. Again using the graphic positioning analogy, the intensity of an emotion may be thought of as represented by its distance from the origin. Consequently, the angular location from the origin can indicate, in this convention, the nature of an emotion which is a composite taken from two scales then being compared, while the distance from the origin is taken to represent the intensity of that emotion.

According to the invention, emotional responses are typically measured on five separate scales, and each is then compared to every other response in a certain sequence. Each response is associated with a characteristic frequency detected by the EEG, namely, 8, 13, 16, 18 and 26 Hertz. The emotions (and their polar opposites) found to correspond to these frequencies respectively are pleasure, arousal, dominance, comprehension and pictorial comprehension. These five responses are sometimes collectively abbreviated "PADCPC". In one of the preferred examples described herein, the amplitude characteristics were taken from the left hemisphere electrode at the 8 Hz, 13 Hz, 16 Hz and 26 Hz frequencies, and at the right hemisphere pickup for 18 Hz signals. These pickup points have shown to provide the most reliable data for measuring the target frequencies which are believed associated with the desired emotional responses, i.e., the emotions of PADCPC.

In the description given herein, and in the claims, the expression "emotional" or words of like import are used to denote a reaction detectable by brain wave activity, without necessarily implying that these responses do not have a rational or intellectual content. Thus, pictorial comprehension and abstract comprehension may not always be properly described as "emotions"; however, for purposes of this invention and for the appended claims, the term "emotion" or the like is intended be broad enough to encompass all of these reactions, i.e., "feelings" as well as understanding.

In other words, for present purposes, a person having greater understanding would be considered to have a different "emotional" state than a person having less understanding, although comprehension or understanding are not often thought of as "emotions." The expression "emotion" as used herein is thus intended to encompass both rational activities, such as comprehension or understanding, and a state of "feelings" such as anger, sorrow, trepidation, etc.

Referring now to a working example of the invention, the apparatus of FIG. 1 was attached to a test subject and prechecked for proper operation. The computer was programmed so as to receive and analyze input from both sides of the scalp midline, feeding the inputs from the left pick up point 14 to the operational amplifier 22 and those from the right portions of the scalp to the amplifier 26. The information received relating to the electroencephalographic signals were fed to the analog-to-digital converters and fed to input ports at the computer. Pursuant to computer instructions, frequencies of 8, 13, 16 and 26 Hz were taken from the left side of the scalp and 18 Hz was monitored by the pick up point from the right side of the scalp.

TABLE 6

| Second | Pleasure Displeasure Left 8 Hz | Abstract Comprehension Left 13 Hz | Arousal Left 16 Hz | Dominance Left 26 Hz | Pictorial Comprehension Right 18 Hz |
|---|---|---|---|---|---|
| 1 | 3.18 | 7.98 | 4.19 | 2.19 | 8.13 |
| 2 | 3.75 | 7.36 | 4.27 | 2.11 | 5.76 |
| 3 | 2.06 | 7.87 | 4.35 | 2.37 | 4.02 |
| 4 | 2.04 | 6.09 | 4.06 | 2.54 | 6.16 |
| 5 | 2.79 | 6.17 | 4.74 | 2.01 | 4.18 |
| 6 | 3.26 | 6.38 | 4.92 | 3.17 | 3.09 |
| 7 | 6.17 | 5.96 | 4.68 | 3.90 | 3.29 |
| 8 | 9.76 | 5.45 | 4.11 | 3.85 | 7.32 |
| 9 | 9.23 | 9.16 | 3.98 | 4.10 | 8.92 |
| 10 | 9.45 | 9.87 | 5.71 | 4.03 | 3.46 |
| 11 | 9.67 | 10.11 | 6.04 | 3.09 | 4.13 |
| 12 | 9.03 | 10.98 | 6.01 | 3.11 | 4.07 |
| 13 | 8.54 | 11.67 | 6.02 | 3.28 | 4.05 |
| 14 | 8.14 | 10.68 | 6.71 | 3.73 | 5.15 |
| 15 | 9.03 | 10.59 | 6.01 | 2.67 | 5.45 |
| 16 | 9.11 | 10.23 | 5.96 | 2.15 | 4.06 |
| 17 | 9.01 | 10.11 | 5.43 | 2.20 | 4.02 |
| 18 | 8.86 | 10.13 | 5.16 | 2.67 | 4.19 |
| 19 | 8.06 | 9.89 | 4.13 | 2.98 | 3.09 |
| 20 | 7.45 | 4.3 | 4.17 | 3.14 | 8.17 |
| 21 | 6.08 | 6.73 | 4.16 | 3.27 | 7.69 |
| 22 | 6.18 | 6.49 | 4.37 | 4.16 | 7.96 |
| 23 | 6.01 | 6.15 | 4.92 | 4.98 | 8.27 |
| 24 | 5.96 | 9.18 | 5.81 | 6.43 | 8.76 |
| 25 | 4.32 | 10.12 | 5.86 | 5.01 | 8.01 |
| 26 | 10.14 | 4.54 | 6.74 | 3.47 | 8.02 |
| 27 | 10.17 | 4.16 | 7.31 | 3.44 | 8.47 |
| 28 | 10.18 | 8.19 | 8.19 | 3.49 | 7.95 |
| 29 | 10.25 | 8.72 | 9.01 | 3.07 | 7.67 |
| 30 | 4.35 | 8.35 | 8.43 | 2.54 | 7.37 |

Utilizing the capacity of the computer, as shown in Table 2, a reading was made during each second of a thirty second audio-visual presentation. In the left hand column of Table 6, the seconds are consecutively numbered from top to bottom. The readings at each of the pick up points, represented as amplitude in micro-volts, were detected and recorded. Thus, merely for example and referring to the 8 Hz frequency activity at the left side scalp pick up point, the voltage varies, beginning with an initial value of 3.18, up to 3.75, down to 2.06 and 2.04, and then begins to rise, etc. as shown by the data, and vary throughout the entire recording period.

The other amplitudes are those set out in the Table. As noted in Table 6, the 8 Hz column relates to activity on the pleasure scale, the 13 Hz frequency to abstract comprehension brain activity, 16 Hz to activity on the arousal scale and dominance to the 26 Hz activity, and the 18 Hz activity representing pictorial comprehension. These values were obtained from a subject that was given an opportunity to see a television commercial that began the first second of time and continued through a 30 second interval.

According to the analysis method, two aspects of these measurements are highly significant. First, each of the frequencies represents a measurement of the target emotion on a numerical or intensity scale of strongly positive to strongly negative.

Some correlations may be thought of in this system as attended by a negative algebraic sign and some a positive sign. Thus, there is a negative correlation between the degree of pleasure and increasing amplitude. At any particular measurement interval, therefore, the lower the amplitude of output waves at 8 Hz, the greater the pleasure at that moment.

There is a positive correlation between signals from the left side of the brain at 13 Hz and comprehension. Thus, to the extent that the amplitude of 13 Hz brain waves at any particular time is high, the level of comprehension is high, with low amplitudes of 13 Hz activity implying a low or decreasing level of comprehension. The left electrode supplying 16 Hz waves produces a positive correlation between arousal and amplitude at that frequency. Thus, a high amplitude at any particular second of time indicates a high level of arousal at that particular instant while a low amplitude indicates a low arousal level. Regarding the 26 Hz activity from the left brain pickup site, the correlation between this amplitude and dominance is negative. However, this could be expressed as a positive correlation between amplitude openness or susceptibility. Thus, where there is high amplitude, the emotion of being open to external influence is great while the amplitude of the 26 Hz frequency is low, a sense of autonomy or self direction increases, such condition being indicative of low susceptibility to outside influence or direction.

Regarding signals from the right side of the brain at 18 Hz, there is a positive correlation between amplitudes of this signal and pictorial comprehension. Thus, as these amplitudes increase, the subjects are experiencing greater ease of visually comprehending the stimuli being instantaneously presented to them. As the amplitude of signals at this frequency decreases, the subject is finding it increasingly difficult to visually comprehend the stimuli being presented.

Inasmuch as considerable data are set out in Table 6, and because the principles of the invention may be illustrated by utilizing a more condensed example, the readings set out in the top third (or first 10 seconds) of Table 6 are reproduced in Table 7, as follows:

TABLE 7

| Second | Pleasure Displeasure Left 8 Hz | Abstract Comprehension Left 13 Hz | Arousal Left 16 Hz | Dominance Left 26 Hz | Pictorial Comprehension Right 18 Hz |
|---|---|---|---|---|---|
| 1 | 3.18 | 7.98 | 4.19 | 2.19 | 8.13 |
| 2 | 3.75 | 7.36 | 4.27 | 2.11 | 5.76 |
| 3 | 2.06 | 7.87 | 4.35 | 2.37 | 4.02 |
| 4 | 2.04 | 6.09 | 4.06 | 2.54 | 6.16 |
| 5 | 2.79 | 6.17 | 4.74 | 2.91 | 4.18 |
| 6 | 3.26 | 6.38 | 4.92 | 3.17 | 3.09 |
| 7 | 6.17 | 5.96 | 4.68 | 3.90 | 3.29 |
| 8 | 9.76 | 5.45 | 4.11 | 3.85 | 7.32 |
| 9 | 9.23 | 9.16 | 3.98 | 4.10 | 8.92 |
| 10 | 9.45 | 9.87 | 5.71 | 4.03 | 3.46 |

Inasmuch as the apparatus and method of the invention are concerned as much with emotional change and change rate as with absolute values, the differences in measured amplitude readings between one second and the reading in the preceding second are termed "marginal values" and are set out in Table 8 as follows:

TABLE 8

| Second | Pleasure Displeasure Left 8 Hz | Abstract Comprehension Left 13 Hz | Arousal Left 16 Hz | Dominance Left 26 Hz | Pictorial Comprehension Right 18 Hz |
|---|---|---|---|---|---|
| 1 | 0.0 | 0.0 | 0.0 | 0.0 | 0.0 |
| 2 | .57 | −.62 | .08 | −.08 | −2.37 |
| 3 | −1.69 | −1.18 | .08 | .26 | −1.74 |
| 4 | −.02 | −1.78 | −.29 | .37 | 2.14 |
| 5 | .75 | .08 | .68 | .37 | −1.98 |
| 6 | .47 | .21 | .18 | .26 | −1.09 |
| 7 | 2.91 | −.42 | −.24 | .73 | .2 |
| 8 | 3.59 | −.51 | −.57 | −.05 | 4.03 |
| 9 | −.53 | 3.71 | −.13 | .25 | 1.6 |
| 10 | .22 | .71 | 1.73 | −.07 | −5.46 |

The above Table 8 shows that, for example, all numbers in the Marginal Values chart begin with zero, since whatever initial reading appears in each column during the first second is considered a base line for purposes of determining marginal values. Subtracting each earlier reading from the immediately following reading in a series of steps gives these marginal values. Thus, where, in the 8 Hz column of Table 7, 3.18 is the micro-volt value of the initial reading, the second reading (3.75 micro-volts) is 0.57 units greater. This number is the marginal value at 8 Hz for second number 2, and therefore appears as the second entry in the left hand column of Table 8. From a value of 3.75, the micro-volt reading drops to 2.06, a difference of −1.69. This figure appears as the third entry in the marginal value table, in the left hand column, and so on for each of the five columns representing different emotional scales. The entire chart is constructed according to these principles.

Table 8, therefore, shows marginal values, over a period of time, for each of the five emotions detected at its characteristic frequency. According to the invention, the determination of an emotional state is made by graphically comparing values on one scale to values on another scale. More particularly, a comparison is made between the marginal or change rate values of one scale with those of another scale. This inventive concept is what is termed "composite emotional force." Composite emotional force, as is shown illustratively in Table 9, is a value that is the algebraic or arithmetic product of two marginal values being compared at a particular time. Thus, in Table 9 below, a value at any particular instant on one scale is multiplied by the value on another scale at that same instant, and the product, termed "composite emotional force," is shown in the right hand column. The "composite emotional force" numbers are rounded but represent the products of the numbers just referred to.

TABLE 9

Composite Emotional Force History - Pleasure/Arousal

| Second | Marginal X (8 Hz, Table 8) | Marginal Y (16 Hz, Table 8) | Product (Composite Emotional Force) (rounded) |
|---|---|---|---|
| 1 | 0.0 | 0.0 | 0.0 |
| 2 | .57 | .08 | .04 |
| 3 | −1.69 | .08 | −.13 |
| 4 | −.02 | −.29 | .01 |
| 5 | .75 | .68 | .51 |
| 6 | .47 | .18 | .08 |
| 7 | 2.91 | −.24 | .70 |
| 8 | 3.59 | −.57 | −2.05 |
| 9 | −.53 | −.13 | .07 |
| 10 | .22 | 1.73 | .38 |

Figure 3:
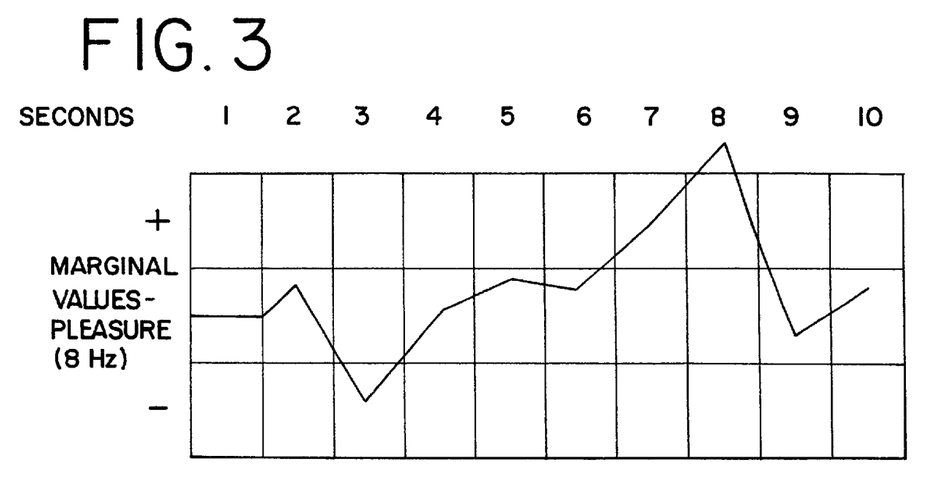
FIG. 3 is a plot of the marginal values of the emotion of pleasure (a frequency of 8 Hz) detected in a subject over a 10 second period, the values comprising such data being processable in accordance with the present invention.
Figure 4:
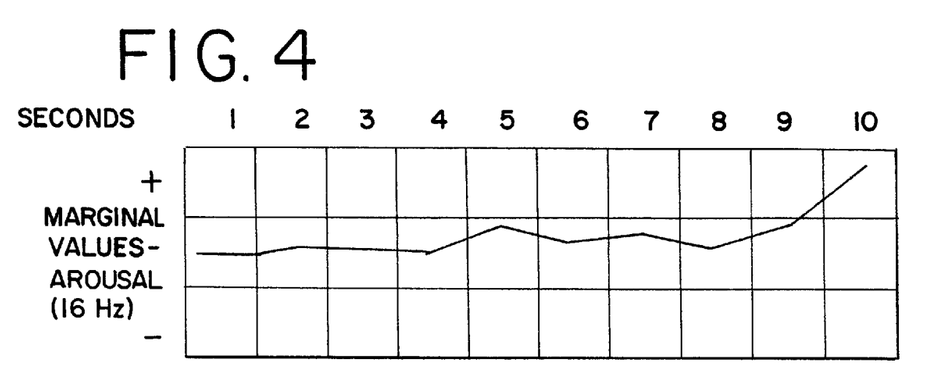
FIG. 4 is a plot of the marginal values of the emotional state of arousal over the same 10 second time period, taken at 16 Hz and being processable in accordance with the invention.
Figure 5:
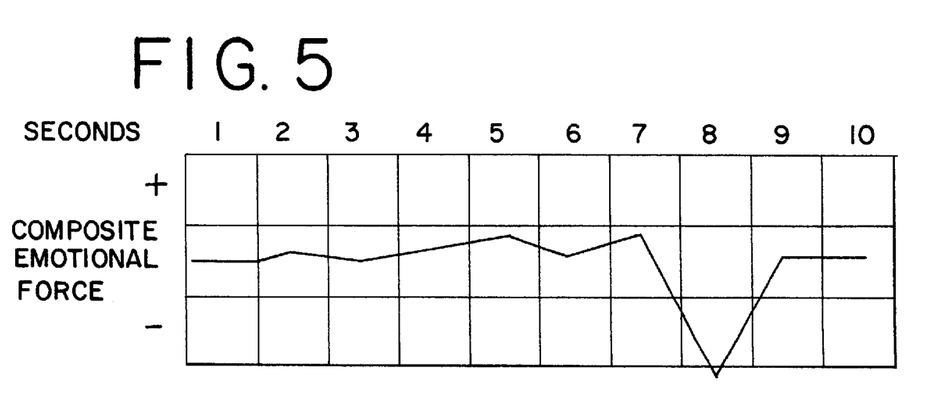
FIG. 5 is a plot of the composite emotional force of the emotions taken at the same time and from the same subject from whom data were taken as reflected in FIGS. 3 and 4, with the plot of FIG. 5 representing the algebraic product of the values taken from the charts of FIGS. 3 and 4.

FIGS. 3–5 in the drawings show charts of selected Marginal Values, namely, Pleasure and Arousal, and what is termed a Composite Emotional Force History based on these two scales. FIG. 3 of the drawings shows the marginal values appearing in the left hand or 8 Hz data column of Table 8. FIG. 4 shows the information appearing in the third data column of Table 8, i.e., the marginal values of "arousal" or 16 Hz values; and FIG. 5 shows what is termed "Composite Emotional Force," or the individual arithmetic products of the series of values shown in the charts of FIGS. 3 and 4. In this connection, reference is made back to Table 9, wherein the values from the first and second data columns of Table 8 are set out as "Marginal X" and "Marginal Y." "X" and "Y" here means that the particular scale is the X or Y axis on a plot of X (8 Hz) versus Y (16 Hz). The third column of Table 9 is entitled "Composite Emotional Force" and represents the arithmetic product of the other two columns, suitably rounded off to two or three significant figures. The algebraic signs of the values follow algebraic conventions, i.e., the products of two positive or two negative numbers creates a positive algebraic sign in the product. If one but not both of the multipliers are negative in algebraic sign, the product is negative.

Referring now to Table 10, there are set out below what is termed a "Composite Emotional Force History." The first row of this chart relates to the values taken from the "Marginal X" or 8 Hz column of Table 9. The largest positive number, 3.59, added to the largest negative number, −1.69, gives a total excursion of 5.3, to the nearest decimal place. Accordingly, the "Range" column of Table 10 shows the maximum excursion total at a given frequency and the "Scale" column shows the average or one-half that value, again to the nearest rounded tenths place number. The "mean" is always zero, since the scale is half the range.

TABLE 10

Composite Emotional Force History

| | Scale | Mean | Range |
|---|---|---|---|
| X | 2.6 | 0 | 5.3 |
| Y | 1.1 | 0 | 2.3 |
| V | 1.3 | 0 | 2.6 |

Figure 6:
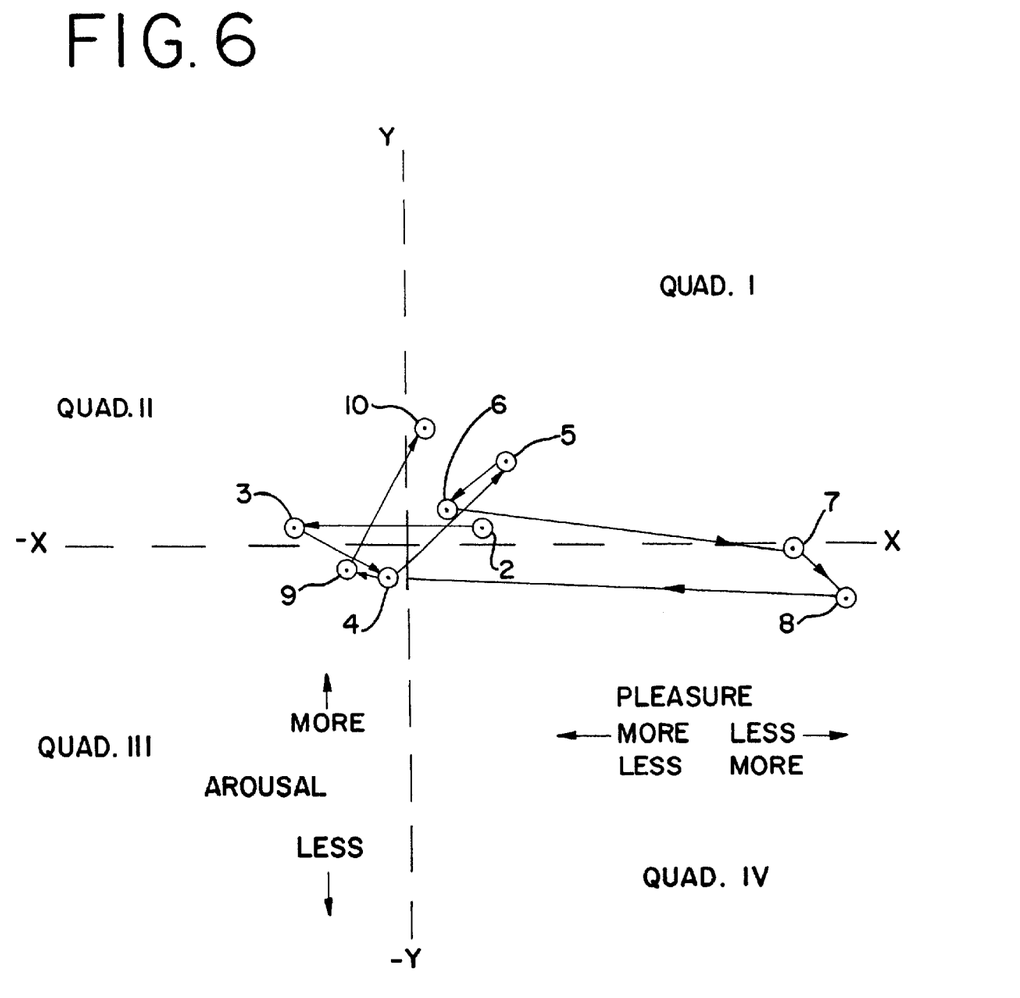
FIG. 6 is a so-called phase plot showing the development of various emotions and emotional intensity over the same 10 second time period depicted in FIGS. 3–5, such plot corresponding to a graphic circumplex of emotions.

Reference is now made to the manner in which these EEG-derived values are used in a non-linear analysis according to the invention. Thus, referring now to FIG. 6 and Tables 9 and 11, which are to be taken together, FIG. 6 represents a so-called "phase plot" of points for the 10 seconds of time just described. The graph of FIG. 6 shows a two-axis display of X and Y marginal values where X is pleasure and Y is arousal. The absolute values of pleasure/arousal are set out in Table 6; the marginal values or changes from one second to the next are different from the absolute values. The marginal values are used in FIG. 6, which shows a numbered series of points, each lying in a particular quadrant and each point being located from the marginal data of Table 9.

From the location of these points, it will be noted that there is an almost random distribution, showing significant emotional differences on the pleasure/arousal scales, which are those being measured during the 10 second interval in question. Some of the points wherein there is a significant excursion from a prior value include point 3, wherein X is strongly negative and Y very slightly positive. only points 5 and 10 show significant positive Y values, while points 5, 7 and 8 show significant positive X values, and point 3 shows a significant negative X value.

As shown in FIG. 6, there are nine plotted points, (2 through 10) each of which by definition falls in one of the four quadrants. The points illustrated are for a 10 second time series, and represent a "phase plot" of pleasure versus arousal, with such emotions undergoing the changes indicated in the graph.

Table 11 identifies each of points 2 through 10 in terms of an angle from the origin, whereas Table 9 identifies the same points in terms of X-Y (Cartesian) coordinates.

TABLE 11

| Second | Angle of Data Point From Origin (degrees) | Corresponding Emotion |
|---|---|---|
| 2 | 10 | Stubborn |
| 3 | 178 | Accepting |
| 4 | 155 | Content |
| 5 | 42 | Hostile |
| 6 | 25 | Irritated |
| 7 | 355 | Indignant |
| 8 | 348 | Unsympathetic |
| 9 | 198 | Serene |
| 10 | 83 | Proud |

Referring now to Table 12, there is shown what is termed an "aggregate emotional profile" of the type wherein a number of subjects are exposed to stimuli and a statistical analysis is made of their response. Thus, in Table 12, time is shown as extending from left to right with there being a column for each of seconds 1 through 10. The vertical column indicates subjects A through J, totalling 10 different subjects, each of whom is subjected to a test observation and data recording in keeping with the invention. Here, the expression "quad visit" relates to the particular quadrant in which a data point is found for that subject at the particular second of time in question.

TABLE 12

Aggregate Emotional Profile

| Seconds | 1 | 2 | 3 | 4 | 5 | 6 | 7 | 8 | 9 | 10 |
|---|---|---|---|---|---|---|---|---|---|---|
| Subject A quad visit | 0 | 1 | 2 | 3 | 1 | 1 | 4 | 4 | 3 | 1 |
| Subject B quad visit | 0 | 1 | 4 | 3 | 1 | 1 | 2 | 1 | 3 | 2 |
| Subject C quad visit | 0 | 2 | 2 | 3 | 1 | 1 | 4 | 2 | 3 | 2 |
| Subject D quad visit | 0 | 1 | 2 | 4 | 2 | 1 | 4 | 4 | 2 | 2 |
| Subject E quad visit | 0 | 3 | 4 | 3 | 1 | 4 | 2 | 4 | 3 | 3 |
| Subject F quad visit | 0 | 1 | 2 | 4 | 1 | 2 | 4 | 4 | 1 | 1 |
| Subject G quad visit | 0 | 4 | 2 | 3 | 4 | 1 | 3 | 4 | 3 | 4 |
| Subject H quad visit | 0 | 1 | 2 | 3 | 3 | 1 | 4 | 4 | 2 | 2 |
| Subject I quad visit | 0 | 3 | 2 | 3 | 1 | 2 | 4 | 3 | 3 | 2 |
| Subject J quad visit | 0 | 1 | 3 | 2 | 1 | 1 | 4 | 3 | 4 | 2 |
| Most Frequent quad visits | 0 | 1 | 2 | 3 | 1 | 1 | 4 | 4 | 3 | 2 |
| Cumulative Profile | 0 | 1 | 2 | 3 | 1 | 1 | 4 | 4 | 3 | 2 |

The quadrants referred to in this table are those found in a graph of the Pleasure/Arousal scale, as was illustrated for example in FIG. 6 and in Tables 9 and 11. The numbers displayed beneath each of the seconds for each subject indicate the particular quadrant wherein the marginal value characterizing the response for that subject was found. Thus, subject "A", in successive time intervals starting with second No. 2, moves to Quadrant 1, then Quadrant 2, Quadrant 3, back to Quadrant for 2 seconds and then spends 2 more seconds in Quadrant 4 before returning through Quadrant 3 to Quadrant 1. Each test subject, A, B, etc. has a counterpart history of having his/her emotions visiting a particular quadrant at a particular time; each subject was, however, viewing identical material over an identical period of time.

A tabulation is then made of the most frequently visited quadrant at each particular second of time as illustrated in the second last line of Table 11. Thus, most of the subjects were in the first quadrant during the second time interval; most were in the second quadrant during the third time interval, etc. The term "aggregate emotional profile" is given to the cumulative responses of all test subjects.

From the use of plurality of subjects, such as 10 or more, the influence of unusual individuals on the response may be tempered or eliminated. Thus, if the test method is utilized to determine the reaction of a particular individual, only that individual need be tested. However, if the purpose of the test is to determine an average, median, or other value with statistically valid frequency measurements, then a number of individuals are tested and the data are analyzed accordingly.

Referring now to the depth of emotional profile available through the use of the invention, inasmuch as each of five different frequencies is used to sample amplitude values, it is possible to create as many as 10 phase plots. In other words, with five variables taken two at a time, 10 combinations are available. For the purpose of most analyses, such as an analysis of advertising matter, it is not necessary to compare all available characteristics, even though it is theoretically possible to do so.

Normally, pleasure, arousal, and dominance are the emotions which are most significant for emotional analysis. Thus, comprehension generally and pictorial comprehension may be valuable analytical tools but are not often in issue with the normally anticipated use of the test material with which the invention is concerned. However, there are specialty applications, such as testing for military or scientific purposes wherein these abilities may be required to be analyzed.

However, by using three scales, and comparing pleasure to arousal, pleasure to dominance, and dominance to arousal, an emotional profile of a subject can be obtained which is quite valuable. Thus, referring to Tables 13, 14 and 15, these characteristics are compared by the methodology just described. Thus, amplitude values are taken at 8 Hz, 16 Hz, and 26 Hz, all from the left side of the head of the test subject.

Comparing dominance and arousal, one compares the amplitude values at 26 and 16 Hz respectively, and the pleasure/dominance phase plots are made comparing the values at 8 Hz to those at 26 Hz. Tables 13–22 do not contain the 100-plus emotions found in the earlier charts, but are concerned only with a more gross or general response of the subject. For this purpose, only the emotions associated with a particular quadrant need to be known. Tables 13–15 shows the dominant emotional character of a subject whose brain waves place him in the illustrated quadrant.

TABLE 13

Pleasure (8 Hz)/Arousal (16 Hz)
Interpretation by Quadrant

| | |
|---|---|
| Quadrant I | This period is marked by a reaction of alarm, hostility, annoyance, disgust, and distrust. Tension is a factor. Arousal is high. |
| Quadrant II | A sense of curiosity and playfulness is present. Energy is increasing along with delight, happiness, and joy. |
| Quadrant III | The response is characterized by a calm, relaxed serenity. Pleasant cheerfulness is creating an agreeable reaction. |
| Quadrant IV | Confusion, bewilderment, and uncertainty mark this periold. Gloomy hopelessness is resulting in boredom. Energy is low. |

TABLE 14

Dominance (26 Hz)/Arousal (16 Hz)
Interpretation by Quadrant

| | |
|---|---|
| Quadrant I | The moment is experienced as highly stimulating. There is a sense of eager enthusiasm for being directed and influenced. |
| Quadrant II | Alert attention is resisting attempts at external influence in favor of strong self-direction. The moment is experienced as perplexing, disgusting, and in strong need of changing. |
| Quadrant III | The current moment is being encountered as pleasant, calm, and relaxed. There is a strong sense of autonomy and inclination to resist attempts of control from external sources. |
| Quadrant IV | The response is markedly sluggish and underaroused. This is resulting in an openness to accept external guidance from any message or event. |

TABLE 15

Pleasure (8 Hz)/Dominance (26 Hz)
Interpretation by Quadrant

| | |
|---|---|
| Quadrant I | Although annoyed, distressed, and resentful the response is submissive to external control. The moment is threatening. |
| Quadrant II | Joyful delight is factoring into an expectancy of being positively influenced. The message is eliciting an agreeable response. |
| Quadrant III | The moment is experienced as cheerfully under control. There is a sense of enthusiasm for expressing influence and control. |
| Quadrant IV | There is an experience of intolerant frustration and anger that is being defiantly expressed in an autonomous dominating need to be in control. |

Tables 16–22 show other combinations which may be made using other frequencies. Each of the Tables 16 through 22 lists the general qualities of the emotions to be found for any particular quadrant when graphically comparing two particular phases.

TABLE 16

Arousal (16 Hz)/Abstract Comprehension (13 Hz)
Interpretation by Quadrant

| | |
|---|---|
| Quadrant I | The moment is being experienced as easily comprehendible and arousing. It is likely that the message is conceived of as astonishing and/or exciting. |
| Quadrant II | While the message is taken as fully comprehended it has evoked a calm, content, and receptive state. |
| Quadrant III | The message is poorly comprehended. It is received with a low level of energy and a sense of caution. |
| Quadrant IV | The message illicits dissatisfaction, is poorly understood and is resulting in increased tension and arousal. |

TABLE 17

Dominance (26 Hz)/Abstract Comprehension (13 Hz)
Interpretation by Quadrant

| | |
|---|---|
| Quadrant I | The moment is perceived as well understood. There is a submissive, open to influence, response to the message. |
| Quadrant II | The moment is perceived as well understood. It evokes a need to resist external influence and exert self-control. |
| Quadrant III | The message is poorly comprehended. It is perceived as confusing. This state of low comprehension evokes a strong sense of independence and resistance to external control. |
| Quadrant IV | The message is poorly comprehended, confusing, and bewildering. This has evoked a sense of dependency on external influence and a willingness to be guided. |

TABLE 18

Pleasure (8 Hz)/Abstract Comprehension (13 Hz)
Interpretation by Quadrant

| | |
|---|---|
| Quadrant I | Although the moment is experienced as fully comprehended it has evoked anger, hostility, and distrust. The object of disgust is perceived as clearly understood. |
| Quadrant II | The message of this period is experienced as fully understood and pleasant. There is an expectation of delight. |
| Quadrant III | The moment is poorly comprehended. Although poorly understood the moment evokes a sense of ease and pleasure. |
| Quadrant IV | The moment is perceived as confusing, uncertain, and lacking clarity. There is a response of gloomy hopelessness and possible boredom. |

TABLE 19

Pleasure (8 Hz)/Pictorial Comprehension (18 Hz)
Interpretation by Quadrant

| | |
|---|---|
| Quadrant I | What is seen is clearly understood. The visual presentation evokes anger, hostility, and disgust. |
| Quadrant II | What is visually perceived is well understood and evokes a strong sense of pleasure and expectation of delight. |
| Quadrant III | The visual panorama is poorly comprehended. Nonetheless there is a sense of calm, ease, and pleasure. |
| Quadrant IV | The current visual picture is confusing. There is a sense of hopelessness and gloom about what is being visually perceived. |

TABLE 20

Arousal (16 Hz)/Pictorial Comprehension (18 Hz)
Interpretation by Quadrant

| | |
|---|---|
| Quadrant I | What is seen is fully comprehended and highly stimulating. |
| Quadrant II | While the visualized material is well understood it evokes little arousal. It is being accepted very passively. |
| Quadrant III | The response to visual material is confusion and sluggish. |
| Quadrant IV | The visual presentation is not well comprehended. It has evoked tension, alertness, and possibly is anxiety provoking. |

TABLE 21

Dominance (26 Hz)/Pictorial Comprehension (18 Hz)
Interpretation by Quadrant

| | |
|---|---|
| Quadrant I | What is being visually perceived is clearly understood. It evokes a submissive openness to external influence or control. |
| Quadrant II | The visual stimuli is clear and well understood. It provokes an autonomous response that is not open to external influence but it rather encourages self-direction. |
| Quadrant III | While visual stimuli is confusing and not clear it has evoked a desire to be influenced by external events and experience self-control. There is no openness to the message. |
| Quadrant IV | The visual stimuli is confusing, perplexing, and poorly comprehended. There is a desire for external influence and guidance. |

TABLE 22

Abstract Comprehension (13 Hz)/Pictorial
Comprehension (18 Hz) Interpretation by Quadrant

| | |
|---|---|
| Quadrant I | Visual stimuli is well understood and integrated in a clear overall understanding of the moment. |
| Quadrant II | While the visual picture is recognized and clearly understood there is a lack of understanding as to how the moment can be integrated into a larger sense of comprehension. |
| Quadrant III | The visual scene is not understood. There is a lack of congruous comprehension about the moment. Confusion is the hallmark of the moment. |
| Quadrant IV | While the visual presentation is poorly comprehended there is a strong sense that the moment of experience is fully understood. |

In connection with the invention, therefore, it will be understood that the invention makes it possible to analyze the emotions of test subjects either in relatively great depth, or in a more sweeping, generalized manner.

In analyzing the emotional reaction of subjects to advertising material, for example, it may only be necessary to determine the particular quadrant in which the emotional response is located, especially if the emotional component is one other than pleasure, arousal or dominance. By determining the quadrant wherein the greatest time is spent in any given duration of emotional response, or in which quadrant the greatest emotional intensity can be found, a correlation between one or more aspects of the subject matter being apprehended and the general nature of that emotion can be established. Thus, the invention makes it possible to determine emotional states with whatever degree of precision is desired for the purpose of observing that particular emotion.

Where more than two or three quadrants are being analyzed, multi-scale analysis will yield a more complex emotional profile then comparing only two scales, and it is always possible for somewhat conflicting emotions to be present. The presence of such emotions and their analysis will rarely if ever involve outright contradiction, but there will be found significant correlation. The concept of multiple phase plots adds depth to the analysis without compromising its overall effectiveness.

A major portion of the foregoing discussion has been directed to describing how an overall emotional profile can be established for one or more subjects who have viewed advertising material. The description illustrates the potential for noting and evaluating the nature and extent of various changes in the emotional state or condition of the subjects as the stimuli are presented to them over a given duration.

The emotional profile that is described in the greatest detail involves, for example, comparisons of the pleasure scale with the arousal scale. Use of these scales is indicated where the tester desires the emotion to be measured to appear in a definite place on the Plutchik circumplex. One reason for using Plutchik's "placements" is reflected in the reference work,[1] which states that the angular placements, each corresponding to a described emotion, are culture-free, reliable, valid descriptors of emotional states. Thus, according to the reference, if the brain wave activity of a person has a certain value at a given instant, then that person is then experiencing the emotion indicated by the chart, regardless of the cultural, economic, ethnic, racial or other character of that particular subject.

[1] *The Psychology and Biology of Emotion* by Robert Plutchik, 1994, pp. 68, 69.

The pleasure/arousal scale and the pleasure/dominance scale are the most commonly used for analyzing things such as television commercials or other materials intended to provide commercial/economic/emotional understanding, response and motivation. However, the use of other frequencies and the making of other comparisons may be indicated depending upon the desires of the tester and the nature of the subject matter being viewed or listened to. Where such inquiries reflect the use of other frequencies, as described, the test material can be used to round out existing profiles, or develop information in entirely different areas.

The material shown to a subject may call for utilizing one or several other scales, however. By way of example, an architect may wish to explore the relation between pictorial comprehension of structures (or renderings of structures) and dominance with respect to a particular design. In other words, comparing just these two scales could indicate whether the subject understands the various aspects of the building design which he is observing and the extent to which he is receptive to such a design.

Contractors, builders, or even product managers may wish to use this approach in what may be termed "packaging" in the broadest sense. In other words, various acceptable forms of housing may be inquired into, as might be the packaging of a consumer product, especially a product that displays a picture of the article to be sold, displays the article itself, as in see-through or "shadow" packaging, or the like.

In the case of a print advertising campaign, the proprietor may choose to examine subjects to determine the extent to which the subject is experiencing abstract comprehension and pleasure. A subject who is capable of identifying headlines, tag lines, or even the content of the entire message, and display a favorable pleasure scale response would indicate that the message has been understood and that it has created a favorable response. Where an advertiser or manufacturer attempts to determine how various subjects experience all or any particular aspect of the content of the intended message in any given medium, measurements are made using comprehension or other appropriate scales. If the proprietor intends to determine whether the content of his message is understood, either in the abstract or in its graphic or pictorial aspects and whether the subject is open to suggestion, a particular emotional scale may be selected for comparison with another scale so that the pairs considered are likely to develop this information.

In the foregoing example set out in the greatest detail, the period or epoch of measurement is described as being one second for short video commercials. The same period or epoch may be appropriate for short audio messages such as radio commercials. For other kinds of content, however, the response interval or epoch may be 3, 5, 10, 15 or 30 seconds or more. If the content being studied is written material, and each of a plurality of paragraphs might reasonably require 15 seconds for reading, then such epochs of a similar duration might be selected. Of course, there may be value changes during this time; however, the values are simply averaged in such a case. For example, if 15 seconds is allocated for the subject to read a paragraph, measuring of the particular emotional scales continues during this whole time and is recorded for analysis; readings applicable to the next increment of the presentation would be made in a subsequent period, usually for an equal duration. Analysis would enable the tester to compare responses to each of the paragraphs or segments.

By way of another example, in vehicle training, including auto and aircraft management, the manufacturer may be interested in the reaction of the respondent to the seating and control panel of the vehicle. An epoch of measurement longer than just a second or two might be indicated because of the length of an acquaintance, orientation or familiarity period. Thus, comprehension could be measured during a comparatively longer duration as the subject successively views the individual element of an instrument panel. Several different forms of panels, each presenting information needed to operate the vehicle, could be viewed in succession, and the maker could then choose the display that was most rapidly comprehended and/or created approval or pleasure in the test subject.

Using a very short span, epoch or duration of measurement might be indicated in the case of an arcade game, for example. Depending on the complexity of the game and/or the interaction between the respondent and the game, the comprehensional analysis might be required to be made from data collected every second or perhaps even in fractions of a second.

A further aspect of the invention involves the possibility of feedback or program variation initiated by he subject, directly or indirectly. Thus, the subject might be required or permitted to use his response to certain stimuli to alter the content of a subsequent portion of the message or other aspect of the presentation being made. This may be considered analogous to, but a much more sophisticated version of, computer-presented information used in other teaching machines or the like wherein the machine questions the subject and determines whether he has given a correct answer, and if so, allows him to proceed to the next operating sequence; if not, he is given more information and asked to try again. The nature of the feedback, according to the present invention, might instead be determined in real time, and the detected emotional component could be arranged to directly control a follow-on presentation or other response without the need to interrogate the subject.

Another application of the inventive principles involves that of making a presentation with the test apparatus positioned on the subject, then making a subsequent presentation, followed by a subsequent test using the equipment in question. Thus, for example, the subject could be exposed for a predetermined time to one or more company names and/or logos, during which time the various components corresponding to different brain wave frequencies would be recorded. Thereafter, such as several hours, days or weeks later, the apparatus is again used on the subject, who is shown the original name or logo. The recall and emotional content of the second test is then compared to the first to determine whether the intervening event changed the perceptions or feelings of the subject.

Using this procedure, by way of example, the subject could be analyzed during the time that a presentation is made identifying the Acme Oil Company and its corporate logo. The response of the subject could be measured while this name and logo are shown, perhaps with other names and logos of competitive companies. The responses of the subject to each of the presentations would be carefully noted, particularly as to comprehension and pleasure.

Subsequently, such as a week or more later, the subject could be given information of a laudatory character describing the cleanliness of restrooms in Acme Service Stations and the courteous service afforded by the company. Subsequent to presentation of that message, during which time the subject's responses would not be monitored, the subject would again be tested merely by showing him the logos and names of one or more of the companies. If for example, the subject were to display a more favorable reaction to the Acme name and logo that was more favorable than that originally elicited simply by showing him the Acme logo without any additional message, the tester could properly assume that the advertising in the intervening time had created a favorable impact on the subject. The test would, in effect, validate the proposition that the advertising had served to create the necessary association between the name and/or logo and the subsequent message that the name and/or logo stood for desirable products or services. If this were true, the tester would know that the advertising was successful.

In most instances, the invention is best utilized to analyze emotional information pertaining to visual presentations, most or all of which customarily include an audio portion. However, the invention is also useful with presentations which have an audio character only, or which may contain relatively abstract information such as a printed word, for example. Thus, "time varying stimuli" or words of like import are sometimes used to describe the most general form of presentation.

In the presently preferred form of apparatus, it is the amplitude of a brain wave signal at a particular frequency that is measured, and the so-called marginal values of these components are determined from changes in these amplitudes or intensities. However, the same or other apparatus may sample similar or different parameters or characteristics of brain waves at a particular frequency, such as power, phase angle, or the like. In any case, the desired parameter is selected so as to be indicative of the intensity or strength of the emotion at the target frequency. Accordingly, as used herein, the expression "amplitude" is to be taken in its general or non-limiting sense, i.e., as indicative of the intensity or strength of a signal of a given frequency at the time in question. The terms "intensity" or "strength" are therefore also sometimes used in the claims.

In the above illustrations, five frequencies were identified and the characteristic set of emotions associated with each such frequency was described. These emotions are sometimes referred to herein and in the claims as "base emotions" or "measurable base emotions" or words of like import, i.e., they are emotions that can be measured as to their presence, absence, and intensity, (including the presence of a polar opposite emotion) by the amplitude or intensity of a brain wave signal at that frequency. The measurable base emotions described included pleasure, arousal, dominance, and pictorial and abstract comprehension.

The more complex emotions able to be experienced by a subject are of concern in the instant method, and the more complex, overall emotional state of a subject that is sought to be determined is referred to herein and in the claims as a "composite emotional state." This state, at any one time, is represented by a coordinate point on a two-axis graph wherein one axis corresponds to one base emotion and the other axis to the other base emotion. Whereas more than two base emotions can be and are measured at one time, the comparisons of the two states or levels are always made two at a time. Points on any such two-axis graph are referred to as "coordinate points," and these points trace the composite emotional state of the subject from time to time.

Of course, the identity of any one graphically determined composite emotion depends on which base emotions are being compared graphically. Although subjects are capable of experiencing many more than the 100 separate emotions identified and referred to, for example, on the "Plutchik Placement" charts, for most purposes, knowledge of the quadrant wherein the coordinate point is located is sufficient to identify a composite emotion. The present invention identifies and/or measures composite emotional states of the subject by using values taken from base emotion measurements, namely those associated with a characteristic frequency. A series of composite emotional states therefore appears as a succession of points on the graph, each individual point lying generally within a certain quadrant on that graph and more particularly, lying a certain distance and direction from the origin.

It will thus be seen the present invention provides new improved methods and apparatus for analyzing neurological response to emotion-inducing stimuli having a number of advantages and characteristics, including those pointed out herein and others which are inherent in the invention. Several preferred methods of practicing the invention having been described by way of illustration, it is anticipated that modifications to the described methods will occur to those skilled in the art and that such modification and changes may be made without departing from the spirit of the invention or the scope of the appended claims.

What is claimed is:

1. A method of determining the extent of the emotional response of a test subject to stimuli in the form of a presentation having at least a time-varying visual content, said method comprising preparing a presentation having stimuli in the form of a time-varying visual content, positioning at least one test subject to observe said presentation including said stimuli for a given duration, establishing a path of communication between said at least one subject and a brain wave detector/analyzer capable of measuring at least an intensity component of each of at least two different brain wave frequencies, each of which is associated with a base emotion, permitting said at least one subject to view said presentation, recording periodic variations in said intensity component of said brain waves at each of the particular frequencies selected, recording the change rates in each of said intensity components periodically during said duration of the presentation, and using said intensity change rate data to construct a graph comprised of plural coordinate points each having a component along each of two axes, with all of said coordinate points graphically establishing the composite emotional state of said subject to said presentation.

2. A method of determining a correlation between a composite emotional state desired to be imparted to a test subject by making an audio visual presentation to said subject and the emotional state actually induced in said subject by making said presentation, said method comprising identifying at least two basic emotion scales, including a pleasure/displeasure scale and an arousal/indifference scale, determining an electroencephalographic brain wave frequency associated with each of said scales, making an audio/visual presentation to at least one test subject while said subject is connected to a brain wave detector/analyzer associated with an electroencephalographic brain wave pickup, noting a variation from time to time in an amplitude of brain waves at each characteristic frequency during the presentation, recording the change rates and directions of said amplitudes at a plurality of intervals during said presentation, and thereafter, using a plot of said amplitude change rates, creating a graph whose points represent coordinate points derived from said changes along a given axis for each of two basic emotion scales, said coordinate points thereby representing on a circumplex display the emotional states of the test subject from time to time.

3. A method of determining whether an advertising presentation affects a test subject exposed to said presentation, said method comprising presenting advertising material having a given content to a subject by way of an audio/visual presentation; selecting at least two frequencies, each characteristic of a measurable base emotion in a human subject and recording the intensity of an electroencephalographic signals having values generated by the subject over a number of sampling intervals during viewing of the presentation, by the subject, recording said values and change rates of said values on a plurality of scales, each corresponding to one of the selected frequencies, graphically determining a composite emotional state of said subject for each sub-interval of a plurality of sub-intervals wherein said presentation is being made, subsequently presenting to the subject advertising material having a content that is different from but is thematically related to the original advertising material; and subsequently recording and analyzing the emotional state of the subject subsequent to the presentation of the thematically related material during a time following said second presentation when portions only of said original presentation are brought to the attention of said subject.

4. A method of altering an advertising presentation having a given content, said method comprising selecting at least one test subject, placing the test subject in communication with an electroencephalographic pick up and brain wave detector/analyzer capable of recording and analyzing spectral data associated with the subject, constructing a composite emotional state profile of the subject using variations of at least two measurable base emotions in the subject, including the emotions of pleasure and arousal, determining whether the composite emotional state of the test subject corresponds to that intended to be imparted by the advertising presentation; noting where the subject has failed to attain the desired emotional state; revising the content of the advertising message in part and retesting the subject using the same methods to determine whether such content changes have succeeded in altering the composite emotional state of said test subject.

5. A method of determining the extent of an emotional response of a test subject to an advertising presentation having audio/visual content, said method comprising preparing a presentation having a time-varying audio/visual content and intended to elicit a particular overall emotional response in an audience to whom viewing said presentation will ultimately be made, positioning at least one test subject in a position to observe said presentation for a given duration, establishing a path of communication between said at least one subject and an electroencephalographic brain wave detector and a brain wave analyzer capable of measuring the intensity of brain wave signals of two different frequencies, a first frequency associated with the emotion of pleasure and a second frequency associated with the base emotion of arousal, permitting said at least one subject to view said presentation and recording the absolute values of brain wave intensity at plurality of intervals during the time when said subject is viewing said presentation, thereby subdividing said presentation into a plurality of sub intervals, thereafter determining the change of intensity and intensity change rates of both selected brain wave frequencies, using the changes of intensity of each point relative to a preceding point to establish values for each of said sub intervals, creating a two-axis, pleasure v. arousal graph having a plurality of coordinate points each representing a pair of the marginal values, one taken from each of said pleasure and arousal scales, and thereafter graphically determining the emotional state of the test subject at each sub interval of the presentation, and an emotional history of the subject during the presentation, and comparing the achieved emotional response of the test subject to the intended response to determine whether changes in the content of the presentation are indicated so as to increase the likelihood that the audience intended to view the presentation will display the intended emotional response.

6. A method as defined in claim 5, wherein said at least one test subject comprises a plurality of test subjects.

7. A method as defined in claim 5, wherein said at least one test subject comprises at least 10 test subjects, and wherein an emotional history of said subjects is determined by statistically analyzing all of said test subjects as a group.

8. A method as defined in claim 5, which further includes measuring the intensity of brain wave signals at a third frequency, said third frequency being associated with dominance, and which further includes creating two additional two-axis graphs, each of said graphs having four quadrants one comparing pleasure and dominance and the other comparing arousal and dominance, and said method also including determining said composite emotional state of said test subject by noting the quadrant in which coordinate points are located and comparing such coordinate points with a predetermined description of the content of such quadrant.

9. A method of determining the extent of an emotional response of a test subject to an advertising presentation, said method comprising preparing a presentation having a time-varying content and intended to elicit a particular overall emotional response in an audience to whom viewing said presentation will ultimately be made, positioning at least one test subject capable of capable of undergoing individual emotional responses each represented by a particular frequency and intensity in a position to observe said presentation for a given duration, establishing a path of communication between said at least one subject and an electroencephalographic brain wave detector and a brain wave analyzer capable of measuring an intensity characteristic of brain wave signals of a plurality of substantially exact but different frequencies, each of said frequencies being associated with a predetermined base emotion, permitting said at least one subject to view said presentation and recording the absolute values of said brain wave intensity characteristic at a plurality of intervals during said duration when said subject is viewing said presentation, thereby subdividing said duration into a plurality of individual time segments, thereafter determining the intensity characteristic changes and intensity characteristic change rates of said plurality of brain wave frequencies, using the changes of said intensity characteristic of each point relative to a preceding point to establish marginal values for each of said time segments, creating at least one two-axis graph, said graph having axes corresponding to two of said base emotions and including a plurality of coordinate points each representing a pair of the marginal values taken from a selected emotion scale, thereafter graphically determining the composite emotional state of the test subject at each segment of the presentation, and comparing the achieved emotional response of the test subject to the response intended to be achieved to determine whether changes in the content of the presentation are indicated so as to increase the likelihood that the audience intended to view the presentation will display the intended emotional response.

10. A method as defined in claim 1, wherein said advertising presentation is a television commercial.

11. A method as defined in claim 1, wherein said advertising presentation is an audio presentation.

12. A method as defined in claim 1, wherein said at least one test subject comprises a plurality of test subjects.

13. A method as defined in claim 1, wherein said at least one test subject comprises at least 10 test subjects.

14. A method as defined in claim 13, which further includes applying statistical analysis to the results of the test subjects.

15. A method as defined in claim 13, wherein a determination of the emotional state of each of said test subjects is made by determining the number and duration of quadrant visits of each of said subjects without precisely determining the emotional state of each of said test subjects.

16. A method as defined in claim 1, wherein said intensity characteristic of said brain wave signals comprises the amplitude of said brain wave signals.

17. A method as defined in claim 1, wherein said plurality of frequencies includes frequencies of 8 Hz, 16 Hz, and 26 Hz.

18. A method as defined in claim 1, wherein said predetermined base emotions are pleasure and arousal.

19. A method as defined in claim 1, wherein said plurality of different frequencies includes five frequencies, the base emotions relating to said frequencies being pleasure, arousal, dominance, comprehension and pictorial comprehension.

20. A method as defined in claim 1, wherein each of said individual time segments comprises a segment of not more than two seconds duration.

21. A method as defined in claim 1, wherein said presentation has a duration of from about 15 seconds to about 1 minute.

22. A method as defined in claim 1, which further includes determining the emotional response of the test subject during presentation and comparing said emotional response of the test subject to the content of the presentation as a method of further analyzing said presentation.

* * * * *